US009387167B2

(12) United States Patent
Perrett et al.

(10) Patent No.: US 9,387,167 B2
(45) Date of Patent: Jul. 12, 2016

(54) ORALLY ADMINISTERED CORTICOSTEROID COMPOSITIONS

(71) Applicant: ADARE PHARMACEUTICALS, INC., Lawrenceville, NJ (US)

(72) Inventors: Stephen Perrett, Princeton, NJ (US); Fredric Jay Cohen, Washington Crossing, PA (US); Gopi Venkatesh, Vandalia, OH (US)

(73) Assignee: ADARE PHARMACEUTICALS, INC., Lawrenceville, NJ (US)

( * ) Notice: Subject to any disclaimer, the term of this patent is extended or adjusted under 35 U.S.C. 154(b) by 0 days.

(21) Appl. No.: 14/311,732

(22) Filed: Jun. 23, 2014

(65) Prior Publication Data

US 2014/0303131 A1 Oct. 9, 2014

Related U.S. Application Data

(62) Division of application No. 12/896,005, filed on Oct. 1, 2010, now Pat. No. 8,771,729.

(60) Provisional application No. 61/247,642, filed on Oct. 1, 2009.

(51) Int. Cl.
 *A61K 9/00* (2006.01)
 *A61K 31/56* (2006.01)
 *A61K 31/569* (2006.01)
 *A61K 45/06* (2006.01)
 *A61K 9/06* (2006.01)

(52) U.S. Cl.
 CPC .............. *A61K 9/0053* (2013.01); *A61K 9/006* (2013.01); *A61K 9/0056* (2013.01); *A61K 9/0065* (2013.01); *A61K 31/56* (2013.01); *A61K 31/569* (2013.01); *A61K 45/06* (2013.01); *A61K 9/06* (2013.01)

(58) Field of Classification Search
 CPC . A61K 31/569; A61K 2300/00; A61K 31/56; A61K 45/06; A61K 9/0053; A61K 9/0056; A61K 9/006; A61K 9/0065; A61K 9/06
 See application file for complete search history.

(56) References Cited

U.S. PATENT DOCUMENTS

| 3,705,172 | A |   | 12/1972 | Buchel et al. |         |
|-----------|---|---|---------|--------------------|---------|
| 3,929,768 | A |   | 12/1975 | Brattsand et al.   |         |
| 4,080,448 | A | * | 3/1978  | Mirsky ............ | 514/171 |
| 4,363,806 | A | * | 12/1982 | Bergstrom et al. . | 514/179 |
| 4,472,393 | A |   | 9/1984  | Shapiro            |         |
| 5,135,740 | A | * | 8/1992  | Katz et al. ...... | 424/401 |
| 5,278,175 | A |   | 1/1994  | Ray et al.         |         |
| 5,403,893 | A | * | 4/1995  | Tanaka et al. .... | 525/218 |
| 5,446,070 | A |   | 8/1995  | Mantelle           |         |
| 5,482,934 | A |   | 1/1996  | Calatayud et al.   |         |
| 5,776,433 | A | * | 7/1998  | Tzou et al. ...... | 424/45  |
| 8,771,729 | B2|   | 7/2014  | Perrett et al.     |         |

| 2001/0006625 | A1 |   | 7/2001 | Bohn et al. |         |
|--------------|----|---|--------|--------------------|---------|
| 2003/0054036 | A1 |   | 3/2003 | Liggins et al.     |         |
| 2003/0099701 | A1 |   | 5/2003 | Takaishi et al.    |         |
| 2004/0053902 | A1 | * | 3/2004 | Smith ............. | 514/171 |
| 2004/0092121 | A1 |   | 5/2004 | Tsai               |         |
| 2004/0106663 | A1 |   | 6/2004 | Talley et al.      |         |
| 2005/0009848 | A1 |   | 1/2005 | Brantl             |         |
| 2005/0112188 | A1 |   | 5/2005 | Elias              |         |
| 2007/0059361 | A1 |   | 3/2007 | Rawas-Qalaji et al.|         |
| 2009/0123550 | A1 | * | 5/2009 | Phillips et al. .. | 424/489 |
| 2009/0123551 | A1 |   | 5/2009 | Phillips           |         |
| 2009/0131386 | A1 |   | 5/2009 | Phillips           |         |
| 2009/0149433 | A1 |   | 6/2009 | Phillips           |         |
| 2009/0169620 | A1 |   | 7/2009 | Venkatesh et al.   |         |

FOREIGN PATENT DOCUMENTS

| CA | 2430481 A1     | 6/2002  |
|----|----------------|---------|
| CL | 3827-2008      | 12/2007 |
| DE | 2323215 A1     | 11/1973 |
| DE | 4129535 A1     | 3/1992  |
| EP | 0057401 A1     | 8/1982  |
| EP | 0440372 A1     | 8/1991  |
| EP | 1595533 A1     | 11/2005 |
| JP | 2003-261439 A  | 9/2003  |
| JP | 2009-519793 A  | 5/2009  |
| JP | 2009-521523 A  | 6/2009  |
| JP | 2009-173552 A  | 8/2009  |
| KR | 2006-0123160 A | 12/2006 |
| WO | 0064450 A1     | 11/2000 |
| WO | 01/19342 A2    | 3/2001  |
| WO | 02/092057 A1   | 11/2002 |
| WO | 03/093344 A1   | 11/2003 |
| WO | 2004/064810 A1 | 8/2004  |
| WO | 20040064810 A1 | 8/2004  |

(Continued)

OTHER PUBLICATIONS

Extended European Search Report, corresponding to European Application No. 10 82 1232.5, dated Feb. 6, 2014; 10 pages.

Korean Office Action (with English Translation), dated Dec. 26, 2013, corresponding to Korean Application No. 10-2012-7010779; 11 total pages.

Georgia Search Report (with English Translation), dated Nov. 28, 2013, corresponding to Georgia Appplication No. AP 2010 012674, 4 total pages.

The Documentary conclusion on (Novelty Examination) Defining the State of the Art (with English Translation), issued by the National Centre of the Intellectual Property of Georgia on Nov. 28, 2013; 7 total pages.

(Continued)

*Primary Examiner* — Aradhana Sasan
(74) *Attorney, Agent, or Firm* — Cooley LLP

(57) ABSTRACT

The present invention is directed to orally administered corticosteroid compositions. The present invention also provides a method for treating a condition associated with inflammation of the gastrointestinal tract in an individual. The method comprises administering to an individual in need thereof a pharmaceutical composition of the present invention.

25 Claims, No Drawings

(56) References Cited

FOREIGN PATENT DOCUMENTS

| WO | 2005/087194 | A1 | 9/2005 |
|----|-------------|----|--------|
| WO | 2007/071179 | A1 | 6/2007 |
| WO | 2007071179 | A1 | 6/2007 |
| WO | 2007/074472 | A2 | 7/2007 |
| WO | 2007074472 | A2 | 7/2007 |
| WO | 2008098634 | A | 8/2008 |
| WO | 2009064819 | A2 | 5/2009 |
| WO | 2009/098595 | A2 | 8/2009 |
| WO | 2009098595 | A2 | 8/2009 |
| WO | 2009123551 | A1 | 10/2009 |
| WO | 2010144865 | A2 | 12/2010 |
| ZA | 6805392 | | 6/1969 |

OTHER PUBLICATIONS

Eurasian Office Action (with English Translation), issued on Oct. 9, 2013, corresponding to Eurasian Application No. 201290171; 5 total pages.
Chinese Office Action (without English Translation), dated Jun. 6, 2014, corresponding to Chinese Patent Application No. 201080047016.8; 8 pages.
Australian Patent Examination Report No. 1, dated May 6, 2014, corresponding to Australian Patent Application No. 2010300550; 3 pages.
New Zealand Examination Report, dated Nov. 13, 2012, corresponding to New Zealand Patent Application No. 599401; 4 pages.
New Zealand Further Examination Report, dated May 29, 2014, corresponding to New Zealand Patent Application No. 599401; 2 pages.
Ukrainian Preliminary Decision on Refusal (with English Translation), dated Jun. 5, 2014, corresponding to Ukraine Patent Application No. A 2012 03919, 7 total pages.
M. Campieri, et al., "Oral Budesonide is as Effective as Oral Prednisolone in Active Crohn's Disease," Gut, vol. 41, 1997, pp. 209-214.
M. Vogt, et al., "Biowavier Monographs for Immediate Release Solid Oral Dosage Forms: Prednisolone," Journal of Pharmaceutical Sciences, vol. 96, Issue 1, 2007; pp. 27-37.
New Zealand First Examination Report, dated Jun. 3, 2014, corresponding to New Zealand Patent Application No. 624922; 3 pages.
Japanese Office Action (without English Translation) corresponding to Japanese Patent Application No. 2012-532304; 4 pages.
Teitelbaum, et al., "Eosinophilic Esophagitis in Children: Immunopathological Analysis and Response to Fluticasone Propionate," Gastroenterology, 2002; vol. 122, pp. 1216-1225.
Pakistan Examination Report corresponding to Pakistan Application No. 839/2010; 1 page.
Colombian Office Action dated Sep. 23, 2014 (with English translation), corresponding to Colombian Application No. 14-105074; 7 pages.
Korean Notice of Office Action dated Oct. 2, 2014 (with English Translation), corresponding to Korean Application No. 10-2014-7017747; 8 pages.
Korean Notice of Decision of Rejection (with English translation), corresponding to Korean Application No. 10-2012-7010779, dated Jan. 2, 2015; 10 total pages.
Taiwanese Office Action (with English translation), corresponding to Taiwanese Application No. 099133628, dated Nov. 24, 2014; 9 total pages.
Eurasian Office Action (with English translation), corresponding to Eurasian Application No. 201290171, dated Oct. 31, 2014; 5 total pages.
Chinese Office Action (with No English translation), issued Dec. 23, 2014 corresponding to Chinese Application No. 201080047016.8; 7 pages.
Saudi Arabian Office Action (with No English translation), issued Jan. 23, 2014, corresponding to Saudi Arabian Application No. 110310734; 4 pages.
English translation of Israeli Examination Report, issued Jan. 20, 2015, corresponding to Israeli Application No. 218928; 3 pages.

Eurasian Search Report (with English translation), issued Jan. 22, 2015, corresponding to Eurasian Application No. 201491358; 4 total pages.
Ukraine Office Action (with English translation), issued Oct. 21, 2014, corresponding to Ukraine Application No. a201203919; 6 total pages.
Korean Office Action (with English translation), issued Nov. 8, 2014, corresponding to Korean Application No. 10-2012-7010779; 10 total pages.
Korean Notice of Decision of Rejection (with English Translation), dated Apr. 21, 2015, corresponding to Korean Patent Application No. 10-2014-7017747; 8 total pages.
Wei et al., "Efficacy of Single-Dose Dexamethasone as Adjuvant Therapy for Acute Pharyngitis" The Laryngoscope, Jan. 2002, 112(1):87-93, Abstract only (1 page).
International Search Report and Written Opinion of the International Searching Authority, dated Feb. 10, 2011, corresponding to international Application No. PCT/US10/50860; 16 total pages.
Merck Index, "Budesonide," 14th Edition, p. 240 (2006) (1 page).
Merck Index, "Ciclesonide," 14th Edition, p. 376 (2006) (1 page).
Merck Index, "Clotrimazole," 14th Edition, p. 407 (2006) (1 page).
Merck Index, "Mometasone Furoate," 14th Edition, pp. 1077-1078 (2006) (2 pages).
Merck Index, "Voriconazole," 14th Edition, p. 1728 (2006) (1 page).
Extended European Search Report, dated Feb. 6, 2014, corresponding to European Application No. 10 82 1232.5; 10 pages.
The Documentary conclusion on (Novelty Examination) Defining the State of the Art (with English Translation), issued by the National Centre of the Intellectual Property of Georgia on Nov. 28, 2013 and Georgia Search Report (with English Translation), dated Nov. 28, 2013, corresponding to Georgia Application No. AP 2010 012674, 11 total pages.
Eurasian Office Action (with English Translation), dated Oct. 9, 2013, corresponding to Eurasian Application No. 201290171; 5 total pages.
Japanese Office Action (with No English Translation) corresponding to Japanese Patent Application No. 2012-532304; 4 pages.
Korean Notice of Decision of Rejection (with English translation), dated Jan. 2, 2015, corresponding to Korean Application No. 10-2012-7010779; 10 total pages.
Eurasian Office Action (with English translation), dated Oct. 31, 2014, corresponding to Eurasian Application No. 201290171; 5 total pages.
Korean Notice of Office Action (with English Translation), dated Oct. 2, 2014, corresponding to Korean Application No. 10-2014-7017747; 8 total pages.
Bower et al., "Manifestations and Treatment of Laryngeal Sarcoidosis". Am. Rev. Respir. Dis, Aug. 1980, vol. 122(2): 325-332 (Abstract Only) 1 page.
Chinese Office Action (with No English Translation), dated Jun. 6, 2014, corresponding to Chinese Patent Application No. 201080047016.8; 8 pages.
Extended European Search Report dated Feb. 9, 2015, corresponding to European Application No. 14184844.0; 7 pages.
English translation of Taiwanese Search Report, dated Nov. 16, 2014, corresponding to Taiwanese Application No. 099133628; 1 page.
Ukraine Decision (with English translation), dated Dec. 26, 2014, corresponding to Ukrainian Application No. A201203919; 7 total pages.
Chilean First Examination Report (with No English translation), dated Jan. 12, 2015, corresponding to Chilean Patent Application No. 2012-000794; 12 pages.
Colombian Office Action dated Sep. 23, 2014 (with English translation), corresponding to Colombian Application No. 14-105074; 7 total pages.
Bower et al., "Manifestations and Treatment of Laryngeal Sarcoidosis". Am. Rev. Respir. Dis, Aug. 1980, vol. 122(2): 325-332. cited byapplicant.
Wei et al., "Efficacy of Single-Dose Dexamethasone as Adjuvant Therapy for Acute Pharyngitis" The Laryngoscope, Jan. 2002, 112(1):87-93, Abstract only.
International Search Report based on international patent application No. PCT/US10/50860, Date of mailing: Feb. 10, 2011.

(56) References Cited

OTHER PUBLICATIONS

Written Opinion of the International Search Authority based on international patent application No. PCT/US10/50860, Date of mailing: Feb. 10, 2011.
Merck Index, "Budesonide," 14th Edition, p. 240 (2006).
Merck Index, "Ciclesonide," 14th Edition, p. 376 (2006).
Merck Index, "Clotrimazole," 14th Edition, p. 407 (2006).
Merck Index, "Mometasone Furoate," 14th Edition, pp. 1077-1078 (2006).
Merck Index, "Voriconazole," 14th Edition, p. 1728 (2006).
International Search Report dated Feb. 2, 2011 and issued in PCT/US10/50860.
Bower et al., "Manifestations and Treatment of Laryngeal Sarcoidosis", Am Rev Respir Dis., Aug. 1980, vol. 122(2), pp. 325-332: abstract only.
Wei et al., "Efficacy of Single-Dose Dexamethasone as Adjuvant Therapy for Acute Pharyngitis", the Laryngoscope, Jan. 2002, vol. 112(1), pp. 87-92.
New Zealand Intellectual Property Office, Further Examination Report, corresponding to New Zealand Application No. 624922, Oct. 14, 2015, pp. 1-2, New Zealand.
Chilean Patent Office, Second Examination Report, corresponding to Chilean Patent Application No. 00794-2012., Sep. 16, 2015, pp. 1-12, Chile.
Taiwan Office Action, Jul. 27, 2015, corresponding to Taiwan Patent Application No. 104107443, p. 1-3.
Taiwan Search Report, May 29, 2015, corresponding to Taiwan Patent Application No. 104107443, p. 1, Taiwan Intellectual Property Office.
Saudi Arabia Office Action, Jul. 29, 2015, corresponding to Saudi Arabia Patent Application No. 114360019, p. 1-5.
Korean Office Action, Notice to Submit Response, Jul. 1, 2015, corresponding to Korean Patent Application No. 10-2015-7008676.
Saudi Arabian First Examination Report (No English translation), issued Mar. 12, 2015, corresponding to Saudi Arabian Patent Application No. 114360019; 7 pages.
Chinese Office Action (No English translation), dated May 12, 2015, corresponding to Chinese Patent Application No. 201080047016.8; 7 pages.
Kumari, et al. "Effect of topical nasal steroid spray in the treatment of non-specific recurrent/chronic pharyngitis—a trial study" Indian J. Otolaryngol. Head Neck Surg. 2008, vol. 60, No. 3 p. 199-201.

\* cited by examiner

ORALLY ADMINISTERED CORTICOSTEROID COMPOSITIONS

CROSS-REFERENCE TO RELATED APPLICATIONS

The present application is a divisional application of U.S. patent application Ser. No. 12/896,005, filed Oct. 1, 2010, and claims priority to U.S. Provisional Application No. 61/247,642, filed Oct. 1, 2009, the disclosures of which is herein incorporated by reference in its entirety for all purposes.

TECHNICAL FIELD OF THE INVENTIONS

This invention relates to orally administered corticosteroid compositions, useful for the treatment of conditions associated with inflammation of the gastrointestinal tract.

BACKGROUND OF THE INVENTION

There are currently no approved topically administered anti-inflammatory medications for the treatment of conditions associated with inflammation of the upper portion of the gastrointestinal tract. One such condition, eosinophilic esophagitis (EE), is an inflammatory condition of the esophagus. It is characterized histologically by a proliferation of eosinophils. The disease is painful, leads to difficulty swallowing and predisposes patients to food impaction and other complications.

Experimental and "off-label" treatments for EE include directing steroid medications formulated and approved for inhalation to the back of the throat such that they are not appreciably inhaled, and instructing the patient to rinse their mouth immediately after administration and not to swallow food or water for two hours after administration. Rinsing is recommended because residual drug in the mouth and throat can lead to candiasis infection, and swallowing is contraindicated because it may wash drug away from the esophagus. Aqueous corticosteroid preparations intended for oral inhalation through nebulization are also mixed with sugars to produce a thickened and sweetened liquid for administration.

Off-label treatments for EE also include administration of corticosteroid tablets containing steroids such as prednisolone. However, systemic administration of corticosteroids is associated with a number of known and undesirable side-effects. For example, oral prednisolone can produce generalized suppression of immune function, and in children, particularly troubling side-effects from long term systemic exposure include growth retardation, which may lead to a reduction in adult height.

There is therefore a need in the art for orally administered corticosteroid formulations which provide topical (rather than systemic) treatment of inflammation of the gastrointestinal tract, particularly inflammation of the upper gastrointestinal tract, such as EE.

SUMMARY OF THE INVENTION

In one embodiment, the present invention is directed to a solid pharmaceutical composition comprising less than or equal to 20 mg of a corticosteroid, wherein the composition has no significant systemic glucocorticoid or mineralcorticoid activity after oral administration, wherein the solid pharmaceutical composition disintegrates within 60 seconds in simulated saliva when tested using the USP <701> Disintegration Test, and/or which disintegrates within 60 seconds when placed in the oral cavity of a human.

In another embodiment, the present invention is directed to a liquid pharmaceutical composition comprising a corticosteroid, and a pharmaceutically acceptable substantially non-aqueous liquid.

In another embodiment, the present invention is directed to a method for treating an inflammatory condition of the gastrointestinal tract. The method comprises administering to an individual in need thereof a pharmaceutical composition of the present invention.

In yet another embodiment, the present invention is directed to a liquid pharmaceutical composition comprising a corticosteroid, a pharmaceutically acceptable aqueous or substantially non-aqueous liquid, and a pharmaceutically acceptable phase change agent dissolved or suspended in the liquid, wherein after administration to a patient, the composition undergoes a change in physical properties upon contact with the gastrointestinal tract of the patient.

In yet another embodiment, the present invention is direction to a composition in solid or liquid form additionally comprising cyclodextrins.

The compositions of the present invention are useful for various conditions including the treatment of inflammatory conditions of the gastrointestinal tract. Accordingly, the present invention also provides a method for treating inflammatory conditions of the gastrointestinal tract in an individual. The method comprises administering to an individual in need thereof a pharmaceutical composition of the present invention.

DETAILED DESCRIPTION OF THE INVENTION

All documents (e.g., patents, patent publication, journal articles, etc.) cited in the present application are incorporated by reference in their entirety for all purposes.

The term "drug", "active" or "active pharmaceutical ingredient" as used herein includes a pharmaceutically acceptable and therapeutically effective compound (e.g., corticosteroid), pharmaceutically acceptable salts, stereoisomers and mixtures of stereoisomers, solvates (including hydrates), and/or esters thereof (e.g., of corticosteroid).

The terms "orally disintegrating tablet", "orally dispersing tablet", or "ODT" refer to a solid dosage form of the present invention, which disintegrates rapidly in the oral cavity of a patient after administration, without chewing. The rate of oral disintegration can vary, but is significantly faster than the rate of oral disintegration of conventional solid dosage forms or chewable solid dosage forms (i.e., tablets or capsules) which are intended to be swallowed immediately after administration. ODT compositions of the present invention can contain pharmaceutically acceptable ingredients which swell, dissolve or otherwise facilitating the disintegration or dissolution of the ODT composition. Such ingredients can include pharmaceutical a disintegrant, a sugar alcohol, a saccharide, or a mixture thereof, a water-soluble binder, a meltable solid (e.g., a wax), which can release the corticosteroid upon entering the stomach, etc.

The term "about", as used herein to refer to a numerical quantity, includes "exactly". For example, "about 60 seconds" includes 60 seconds, exactly, as well as values close to 60 seconds (e.g., 50 seconds, 55 seconds, 59 seconds, 61 seconds, 65 seconds, 70 seconds, etc.). When the term "about" is used in reference to a range of values, the term "about" refers to both the minimum and maximum value of the range (e.g., "about 1-50 µm" means "about 1 µm to about 50 µm").

The term "adhesive agent", as used herein refers to agents which promote adhesion of the corticosteroid to biological surfaces, and includes, but is not limited to bio-adhesive agents. Adhesive agents can include compounds which adhere to the oropharyngeal mucosa, as well as compounds which increase the residence time of the compositions of the present invention on the oropharyngeal mucosa of a patient.

The term "intimately associated", as used herein to describe the spatial relationship between two or more components of a composition refers to components that are intimately mixed, such as for example in mixtures, coatings and matrices.

The term "having no significant systemic glucocorticoid or mineralocorticoid activity", as used herein refers to corticosteroid compositions which do not provide a generalized effect in the body through absorption into the circulation, but do provide local effects through topical contact with a diseased tissue. Corticosteroids which have high systemic glucocorticoid potencies when administered orally include e.g., hydrocortisone, prednisone, prednisolone, methylprednisolone, dexamethasone, betamethasone, etc.) or mineralocorticoid potencies (e.g., alsosterone). These corticosteroids may be suitable for use in the compositions of the present invention if they are used at a sufficiently low dose, or are otherwise formulated such that they do not have significant systemic glucocorticoid or mineralcorticoid activity. Exemplary corticosteroids suitable for use in the compositions of the present invention include, but are not limited to budesonide, fluticasone, flunisolide, ciclesonide, mometasone, beclomethasone and tixocortol.

The term "bio-gelling polymer" as used herein refers to a polymer forms a gel under GI tract physiological conditions, for example, upon contact with physiological fluids or at physiological temperature.

The term "substantially non-aqueous liquid" refers to liquids which are completely anhydrous, or include only small amounts of water (e.g. less than about 10% water, for example less than about 9%, less than about 8%, less than about 7%, less than about 6%, less than about 5%, less than about 4%, less than about 3%, less than about 2%, or less than about 1% water).

The term "phase change agent" refers to an agent which, upon dissolution or suspension in the substantially non-aqueous liquids of the present invention, causes the liquid pharmaceutical compositions of the present invention to undergo a change in physical properties after administration to a patient. For example such changes in physical properties include precipitation of the dissolved or suspended components of the composition (e.g. the corticosteroid, optional excipients, and the phase change agent); gelation of the composition (e.g., formation of a hydrogel of the phase change agent and optionally excipients, wherein the hydrogel comprises at least a portion of the corticosteroid); or an increase in viscosity of the composition. These changes in physical properties have the effect of increasing or enhancing contact of the corticosteroid to the mucosa of the gastrointestinal tract of the patient.

Unless indicated otherwise, all percentages and ratios are calculated by weight. Unless indicated otherwise, all percentages and ratios are calculated based on the total composition.

The solid and liquid pharmaceutical compositions of the present invention are suitable for topical administration of a corticosteroid to the gastrointestinal tract, for example the upper gastrointestinal tract such as the esophagus. Topical administration of a corticosteroid for conditions associated with inflammation of the gastrointestinal tract is desirable because it results in fewer side-effects than systemic corticosteroid administration. Such side-effects are reduced still further with the use of corticosteroids which do not have significant systemic glucocorticoid or mineralocorticoid activity because of their reduced systemic exposure.

The pharmaceutical compositions of the present invention are suitable for treating inflammatory conditions of the gastrointestinal tract, for example inflammatory conditions of the upper gastrointestinal tract such as the esophagus. Thus, the present invention includes treating inflammatory conditions of the gastrointestinal tract by administering to a patient in need thereof a solid or liquid pharmaceutical composition of the present invention. Inflammatory conditions of the gastrointestinal tract which may be treated according to the present invention include inflammation of the esophagus, inflammation of the glottis, inflammation of the epiglottis, inflammation of the tonsils, inflammation of the oropharynx, eosinophilic esophagitis, gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis (also known as medication esophagitis), persistent drug-induced esophagitis, Crohn's disease of the esophagus, scleroderma, and scleroderma sine scleroderma, systemic lupus erythematosus, systemic vasculitides, leukocytoclastic vasculitis, polyarteritis nodosa, Churg-Strauss syndrome, rheumatoid vasculitis, and pseudomembranous esophagitis.

In other embodiments, the pharmaceutical compositions of the present invention are suitable for treating inflammatory conditions of the gastrointestinal tract such as an autoimmune disease, Behcet's syndrome, Kawasaki disease, X-linked lymphoproliferative syndrome; an infectious viral disease caused by one or more of the following viruses: Adenoviridae, Coronaviridae, Coxsackie virus, Herpes simplex, HIV, Influenza (Type A), Lassa virus, Epstein-Barr virus, Parainfluenza, or Respiratory syncytial virus; an infectious bacterial disease caused by one or more of the following bacteria: *Arcanobacterium hemolyticum*, *Chlamydia* (*Chlamydophila*), *Corynebacterium*, *Francisella tularensis*, Group A, C, G *Streptococcus*, *S. pneumoniae*, *S. pyogenes*, *Haemophilus influenza* type B, *Mycoplasma pneumonia*, *Neisseria gonorrhea*, Multiple (e.g. peritonsillar cellulitis/abscess); an infectious fungal disease caused by *Candida* (e.g. *Candida albicans*) or *Histoplasma* (e.g. *H capsulatum*); inflammation caused by injury or an irritant selected from the group consisting of an airway foreign body, chloroacetophenone, chlorobenzylidene malononitrile, chronic smoke exposure, morpholine, sulfuryl fluoride, and scalded throat; lepidopterism, Seasonal allergic pharyngitis, and Stevens-Johnson syndrome; or periodic fever; etc.

In one embodiment, the present invention includes a method for treating inflammation of the esophagus comprising administering to a patient in need thereof a pharmaceutical composition of the present invention. In one such embodiment, the present invention includes a method for treating eosinophilic esophagitis comprising administering to a patient in need thereof a pharmaceutical composition of the present invention.

In another embodiment, the present invention includes a method for treating gastroesophageal reflux disease (GERD), nonerosive reflux disease (NERD) or erosive esophagitis comprising administering to an individual in need thereof a pharmaceutical composition of the present invention.

In another embodiment, the present invention includes a method for treating a food allergy with an identified allergen, e.g., "atopic IBS", and "atopic bowel".

In one embodiment, the present invention provides a solid pharmaceutical composition which comprises less than or equal to 20 mg of a corticosteroid, wherein the composition has no significant systemic glucocorticoid or mineralocorticoid activity, and wherein the solid pharmaceutical composition disintegrates within 60 seconds in simulated saliva when tested using the USP <701> Disintegration Test. In another embodiment, the solid pharmaceutical compositions of the present invention disintegrate within 60 seconds in the oral cavity of the patient, e.g. human. In still other embodiments, the solid pharmaceutical compositions of the present invention disintegrate within 30 seconds in simulated saliva (using the USP <701> Disintegration Test), or in the oral cavity of a patient. In still other embodiments, the solid or liquid pharmaceutical compositions of the present invention topically provide a therapeutically effective amount of a corticosteroid to inflamed tissues of the gastrointestinal tract, after oral administration to a patient in need thereof.

Solid pharmaceutical compositions of the present invention can include, for example, an ODT (as described herein), a wafer, a film, or other solid dosage form which disintegrates or dissolves rapidly in the mouth to form a solution or dispersion of a corticosteroid, which can readily be swallowed.

In another embodiment, the present invention provides a liquid pharmaceutical composition comprising a corticosteroid and a pharmaceutically acceptable solvent, wherein the liquid pharmaceutical composition has no significant systemic glucocorticoid or mineralocorticoid activity. In one such embodiment the composition also includes a pharmaceutically acceptable bio-gelling polymer dissolved in the solvent, and the composition increases in viscosity upon contact with the gastrointestinal tract of an individual. In other embodiments, the liquid compositions of the present invention comprise a corticosteroid complex with a cyclodextrin, typically suspended or dissolved in a liquid carrier. The liquid compositions of the present invention may be in the form of a solution or a suspension. Liquid pharmaceutical compositions according to the present invention are compositions which are liquids at standard temperature and pressure conditions.

Suitable pharmaceutically acceptable liquids which may be used in the liquid pharmaceutical compositions of the present invention include, for example, alcohols, oils, glycols, glycol ethers, pyrrolidones, polyethylene glycols, N-methyl-2-pyrrolidone (NMP), 2-pyrrolidone, glycerol, tetraglycol, glycerol formal, solketal, ethyl acetate, ethyl lactate, ethyl butyrate, dibutyl malonate, tributyl citrate, tri-n-hexyl acetylcitrate, diethyl succinate, diethyl glutarate, diethyl malonate, triethyl citrate, triacetin, tributyrin, diethyl carbonate, propylene carbonate, acetone, methyl ethyl ketone, dimethyl sulfoxide, dimethyl sulfone, tetrahydrofuran, caprolactam, N,N-diethyl-m-toluamide, 1-dodecylazacycloheptan-2-one, 1,3-dimethyl-3,4,5,6-tetrahydro-2(1H)-pyrimidinone, and combinations thereof. In one embodiment, the liquid is selected from the group of alcohols, oils, glycols, glycol ethers, pyrrolidones, polyethylene glycols, glycerol and combinations thereof. In one such embodiment, the liquid is selected from the group of ethanol, glycerol, propylene glycol, glycerides, polyethylene glycol with a molecular weight between about 200 and 600, and combinations thereof. In other embodiments, the liquid pharmaceutical compositions of the present invention can comprise aqueous suspensions or solutions of a corticosteroid.

In one embodiment the bio-gelling polymer is a thermosensitive polymer. Suitable thermosensitive polymers include polyacrylamides, such as poly(N-isopropylacrylamide), as well as poly(ether-ester) copolymers, such as poly (ethylene glycol-(DL-lactic acid-co-glycolic acid)-ethylene glycol). Such thermosensitive polymers can precipitate or cause an increase in viscosity of the liquid compositions of the present invention upon administration to a patient, and subsequent warming in the gastrointestinal tract. Thus, the compositions of the invention precipitate on or have a longer residence time on the gastrointestinal mucosa the patient, thereby increasing the topical contact of the corticosteroid on the gastrointestinal mucosa. Consequently, the contact of the corticosteroid with the gastrointestinal mucosa is enhanced and/or prolonged.

In another embodiment, the compositions of the present invention include a bioadhesive agent, which is a lipid or a mixture of lipids. Such lipids or lipid mixtures may undergo a phase transition on contact with wetted biological surfaces to form an adhesive film. Examples of such lipids include mixtures of so-called membrane and non-membrane lipids which will typically form lamellar and non-lamellar structures, such as hexagonal or cubic phases, respectively. Examples of such lipids are glycerphospholipids such as phosphatidyl choline, and diacyl glycerols such as glycerol dioleate. Such self-organizing structures demonstrate superior spreading and adhesion to biological surfaces and have the advantage or being pharmaceutically acceptable materials. Advantageously the active agent, e.g. a corticosteroid may be dissolved in the lipid component.

Suitable non-aqueous solvents which may be included in the liquid pharmaceutical compositions of the present invention include pharmaceutically acceptable non-aqueous solvents in which the particular bio-gelling polymer is soluble. For example, the solvent may be an alcohol (e.g., ethanol), N-methyl-pyrrolidone (NMP), glycerol, propylene glycol, liquid polyethylene glycol, diethylene glycol monoethyl ether and mixtures thereof. In certain embodiments the solvent is water-miscible and the bio-gelling polymer is water-insoluble, so that upon administration the solvent mixes rapidly with the water from the digestive tract of the patient, causing the bio-gelling polymer and corticosteroid to precipitate on the gastrointestinal mucosa of the patient. Consequently, the contact of the corticosteroid with the gastrointestinal mucosa is enhanced and/or prolonged.

Other bio-gelling polymers which may be included within the liquid pharmaceutical compositions of the present invention include cellulose derivatives (e.g., esters and/or ethers, crosslinked cellulose esters and/or ethers) cellulose esters, methacrylic acid and methacrylate polymers, polylactides, polyglycolides, polycaprolactones, polydioxannones, polycarbonates, polyhydroxybutyrates, polyalkyene oxalates, polyanhydrides, polyamides, polyesteramides, polyurethanes, polyacetals, polyketals, polyorthocarbonates, polyphosphazenes, polyhydroxyvalerates, polyalkylene succinates, poly(malic acid), poly(amino acids), chitin, chitosan, polyorthoesters, and copolymers, terpolymers and mixtures thereof. Bio-gelling polymers swell, and/or form hydrogels upon contact with moisture in the gastrointestinal tract, thereby adhering or increasing the viscosity of the compositions of the present invention on the mucosa of the gastrointestinal tract. Consequently, the contact of the corticosteroid with the gastrointestinal mucosa is enhanced and/or prolonged.

In certain embodiments, the liquid pharmaceutical compositions of the present invention increase in viscosity upon contact with the gastrointestinal tract of an individual. In one embodiment, the increase in viscosity is at least 50% (relative to the viscosity prior to administration). In another such embodiment, the increase in viscosity is at least 100%. In yet another such embodiment, the increase in viscosity is at least 200%. The viscosity of the compositions before contact with the gastrointestinal tract of an individual may be measured using a viscometer. The change in viscosity of the compositions upon contact with the gastrointestinal tract of an individual may be determined by measuring the viscosity of the composition under simulated physiological conditions. For example, the viscosity of a given composition may be measured in simulated saliva.

Suitable corticosteroids which may be included in the pharmaceutical compositions of the present invention include budesonide, fluticasone, flunisolide, ciclesonide, mometasone, beclomethasone, tixocortol and salts, solvates, and esters thereof. In a particular embodiment, the compositions of the present invention comprise fluticasone. In other embodiments, the compositions of the present invention comprise budesonide. Corticosteroids which typically have systemic glucocorticoid or mineralocorticoid activity when administered orally can also be used in the compositions of the present invention, if the composition is modified to reduce or suppress systemic uptake of the corticosteroid.

The amount of corticosteroid present in the pharmaceutical compositions of the present invention will depend upon the particular corticosteroid utilized. In general, however, the amount will be selected so as to maximize the therapeutic benefit from topical administration while minimizing systemic absorption. In the case of solid pharmaceutical compositions of the present invention, the amount of corticosteroid in the composition typically is less than or equal to 20 mg. In one embodiment the amount of corticosteroid in the pharmaceutical composition is between about 0.01 mg and about 20 mg. In another embodiment the amount of corticosteroid in the pharmaceutical composition is between about 1 mg and about 15 mg. In still another embodiment the amount of corticosteroid in the pharmaceutical composition is between about 2 mg and about 10 mg. In yet another embodiment the amount of corticosteroid in the pharmaceutical composition is between about 2 mg and about 5 mg. In still other embodiments, the amount of corticosteroid is about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 90 mg, or about 20 mg, inclusive of all ranges and subranges therebetween.

Typical amounts of corticosteroid in the solid pharmaceutical compositions of the present invention include about 0.25 mg, about 0.5 mg, about 1 mg, about 1.5 mg, about 2 mg, about 2.5 mg, about 3 mg, about 3.5 mg, about 4 mg, about 4.5 mg and about 5 mg. In the case of liquid pharmaceutical compositions of the present invention, the concentration of corticosteroid in the composition typically is such that an amount of corticosteroid consistent with the amounts described above (i.e., 0.01 mg to 20 mg) may be conveniently administered to an individual. For example, the concentration of corticosteroid may be such that a single pump from a spray pump device delivers about 0.05 mg, or any other therapeutically effective pre-selected amount, of corticosteroid to the oral cavity of an individual. In a particular embodiment, the compositions of the present invention comprise about 0.25 mg of fluticasone.

Upon administration of a solid pharmaceutical composition of the present invention to an individual, the composition disintegrates in the patient's oral cavity. In one embodiment, the composition of the present invention is in the form of an ODT. An ODT comprises drug containing particles (e.g., a corticosteroid as described herein optionally coated or combined with an adhesive agent as described herein), combined with rapidly dispersing microgranules. Rapidly dispersing microgranules can be prepared as described in US 2005/0232988 or US 20010014340 by granulating a disintegrant having an average particle size of not more than about 30 μm with a sugar alcohol and/or saccharide having an average particle size of not more than about 30 μm. The granulation can be carried out, for example, in a high shear granulator with approximately 20-25% water as the granulating fluid, and if needed wet milled and dried to produce rapidly dispersing microgranules having an average particle size of not more than about 300 μm (e.g., about 175-300 μm).

The ratio of the disintegrant to the sugar alcohol, saccharide, or mixture thereof in the rapidly dispersing microgranules ranges from about 90/10 to about 99/01, for example about 90/10, about 91/9, about 92/8, about 93/7, about 94/6, about 95/5, about 96/4, about 97/3, about 98/2, about 99/1, inclusive of all values, ranges, and subranges therebetween.

The ratio of the rapidly dispersing microgranules to drug-containing particles ranges from about 5/1 to about 1/1, including about 5/1, 4/1, 3/1, 2/1, 1/1, inclusive of all values, ranges, and subranges therebetween.

The corticosteroid containing particles of the ODT dosage form should also have a small enough particle size such that after disintegration of the ODT in the oral cavity of the patient, a smooth, easy-to-swallow suspension results. In most embodiments in which the pharmaceutical compositions of the present invention is provided as an ODT dosage form, the average particle size of the taste-masked non-opioid analgesic/opioid analgesic drug-containing microparticles is not more than about 400 μm, or in some embodiments not more than about 300 μm.

The ODT dosage form as described herein may also include pharmaceutically acceptable excipients typically used in disintegrating tablet formulations such as microcrystalline cellulose and spray dried mannitol (compressible diluents), croscarmellose sodium or crospovidone (super disintegrant), coloring agents, and optionally magnesium stearate or sodium stearyl fumarate (lubricant intragranularly mixed or used externally to lubricate die and punch surfaces).

Tablet dosage forms, including ODT dosage forms, comprising the pharmaceutical composition of the present invention have a low friability, e.g., less than about 1%, (e.g., less than about 0.9%, less than about 0.8%, less than about 0.7%, less than about 0.6%, less than about 0.5%, less than about 0.4%, less than about 0.3%, etc., inclusive of all ranges and subranges therebetween) in order to have sufficient durability to withstand handling, shipping, and/or packaging in push-through blister packaging.

A non-limiting list of suitable disintegrants for the rapidly dispersing microgranules includes crospovidone (cross-linked PVP), sodium starch glycolate, cross-linked sodium carboxymethylcellulose, calcium silicate, and low substituted hydroxypropyl cellulose. The amount of disintegrant in the ODT is typically in the range of about 1% to about 10% by weight.

A non-limiting list of suitable sugar alcohols includes mannitol, sorbitol, xylitol, maltitol, arabitol, ribitol, dulcitol, iditol, isomalt, lactitol, erythritol and combinations thereof. A non-limiting list of suitable saccharides includes lactose, sucrose, maltose, and combinations thereof. The amount of sugar alcohol and/or saccharide in the ODT ranges from about 30% to about 70% by weight.

Pharmaceutically acceptable excipients include fillers, diluents, glidants, disintegrants, binders and lubricants. Other pharmaceutically acceptable excipients include acidifying agents, alkalizing agents, preservatives, antioxidants, buffering agents, chelating agents, coloring agents, complexing agents, emulsifying and/or solubilizing agents, flavors, perfumes, humectants, sweetening agents and wetting agents.

Examples of suitable fillers, diluents and/or binders include lactose (e.g. spray-dried lactose, α-lactose, β-lactose, Tabletose® various grades of Pharmatose®, Microtose® or Fast-Flo®), microcrystalline cellulose (various grades of Avicel®, Ceolus®, Elcema®, Vivacel®, Elcema®, Vivacel®, Ming Tai® or Solka-Floc®), hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate and collagen.

Examples of suitable diluents include e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose and sugar.

Examples of suitable disintegrants include e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, and carboxymethyl starch (e.g. Primogel® and Explotab®).

Specific examples of glidants and lubricants include stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate and sodium acetate.

Other excipients include e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents and agents for modified release.

Other functional excipients such as cyclodextrins may be used, for example as taste-masking agents (e.g., by means of their complexation with the corticosteroid). Cyclodextrins may also be used as a carrier and/or a dispersant to facilitate delivery and distribution of the corticosteroid at the intended site of therapeutic activity.

Compositions of the present invention in the form of an ODT disintegrate into corticosteroid containing particles while sugar alcohol/saccharide-containing granules included within the composition rapidly dissolve, thereby forming a smooth suspension that can be readily swallowed.

Other corticosteroid-containing orally disintegrating or orally dissolving dosage forms such as wafers or films can also be used. For example, wafers can include dried or lyophilized compositions such as orally disintegrating or dissolving dosage forms prepared using Zydis® lyophilization technology (e.g., as described in U.S. Pat. No. 6,316,027), containing a corticosteroid as the active pharmaceutical ingredient. Film dosage forms can include edible films such as those described in U.S. Pat. No. 6,596,298 or U.S. Pat. No. 6,740,332, containing a corticosteroid as the active pharmaceutical ingredient.

The rate of disintegration of the compositions of the present invention in the oral cavity of an individual can be on the order of about 60 seconds or less, about 50 seconds or less, about 40 seconds or less, about 30 seconds or less, about 20 seconds or less, or about 10 seconds or less.

The rate of disintegration of the solid pharmaceutical compositions of the present invention can be measured using various in vitro test methods, for example the USP <701> Disintegration Test. When using the USP <701> Disintegration Test, the rate of disintegration of the compositions of the present invention typically is about 60 seconds or less, about 45 seconds or less, about 30 seconds or less, about 20 seconds or less, or about 10 seconds or less.

In other embodiments, the solid pharmaceutical compositions of the present invention can have any rate of disintegration or dissolution in the oral cavity of a patient which provides a therapeutically effective amount of corticosteroid to the inflamed tissues of the gastrointestinal tract. For example, in some embodiments, solid pharmaceutical compositions according to the present invention include compositions that provide about 0.5 mg to about 20 mg of the corticosteroid to the inflamed tissues of the gastrointestinal tract after oral administration.

In one embodiment, the solid pharmaceutical compositions of the present invention include an adhesive agent. Suitable adhesive agents include sucrose aluminum sulfate complex, chitosan and derivatives thereof (e.g., trimethylchitosan, chitosan salts), polyvinylpyrrolidone, methylcellulose, sodium carboxymethylcellulose, hydroxypropyl cellulose, cross-linked or uncross-linked polyacrylates, cross-linked polyacrylates, acidic cross-linked or uncross-linked polyacrylates, polyacrylic acid homopolymers or copolymers, aminoalkyl methacrylate copolymers, methacrylic acid/methylmethacrylate copolymer, alkylacrylate/alkylmethacrylate copolymers, ammoniomethacrylate copolymers, Eudragit® polymers (E, L, S, NE, RL, and RS grades), carbomer homopolymers or copolymers, hydrophilic polysaccharide gums, maltodextrins, cross-linked alignate gum gels, polycarboxylated vinyl polymers, pectins, xanthan gums, alginic acid, modified alginic acids, and combinations thereof.

In certain embodiments of the solid pharmaceutical compositions of the present invention, the corticosteroid and the adhesive agent are intimately associated. In one such embodiment the solid pharmaceutical composition comprises corticosteroid surrounded or encapsulated by the adhesive agent. In another such embodiment the solid pharmaceutical composition comprises corticosteroid disposed on the surface of the adhesive agent. In still other embodiments, the solid pharmaceutical composition comprises corticosteroid mixed or granulated with the adhesive agent.

Topical administration of a corticosteroid to the oral cavity of individuals has been associated with candidiasis infection. Consequently, in one embodiment pharmaceutical compositions of the present invention include an antifungal agent. Suitable antifungal agents include, but are not limited to mitotic inhibitor antifungals, pyrimidine analog antifungals, polyene antifungals, benzimidazole antifungals, imidazole antifungals, polyene antifungals, triazole antifungals, thiazole antifungals, allylamine antifungals, echinocandin antifungals, and other "uncategorized" antifungals recognized in the art that do not fall within any of the above categories (e.g., tolnaflate and ciclopirox). For example, suitable antifungal agents which may be included in the solid pharmaceutical compositions of the present invention include abafungin, amorolfine, anidulafungin, bifonazole, butenafine, butoconazole, candicin, caspofungin, ciclopirox, clotrimazole, econazole, fenticonazole, filipin, fluconazole, flucytosine, griseofulvin, isavuconizole, isoconazole, itraconazole, ketoconazole, micafungin, miconazole, miconazole nitrate, naftifine, natamycin, nystatin, oxiconazole, posaconazole, pramiconazole, ravuconazole, rimocidin, setaconizole, sulconazole, terbafine, terconazole, tioconazole, tolnaftate, undecylenic acid, and voriconazole.

In another embodiment, pharmaceutical compositions of the present invention include an antiviral agent. Antiviral agents which may be included in the solid pharmaceutical compositions of the present invention include interferons, nucleoside and nucleotide reverse transcriptase inhibitors, non-nucleoside reverse transcriptase inhibitors, protease inhibitors, integrase inhibitors, fusion inhibitors, maturation inhibitors, guanosine analogs, puridine analogs, pyrimidine analogs, and other "uncategorized" antiviral drugs recognized in the art which do not fall within any of the above classes (e.g. foscarnet and miltefosine). For example, suitable antifungal agents which may be included in the solid pharmaceutical compositions of the present invention include abacavir, aciclovir (also known as acyclovir), adefovir, amantadine, amdoxovir, amprenavir, aplaviroc, apricitabine, arbidol, atazanavir, bevirimat, BMS-488043, boceprevir, brivudine, cidofovir, DCM205, docosanol, delavirdine, didanosine, durunavir, efavirenz, elvitegravir, elvucitabine, emtricitabine, enfuvirtide, epigallocatechin gallate, etravirine, famciclovir, fosamprenavir, ganciclocvir, globoidnan A, griffithsin, ibalizumab, idoxuridine, indinavir, lamivudine, lopinavir, loviride, maraviroc, nelfinavir, nevirapine, oseltamivir, pegylated interferon α-2a, pegylated interferon α-2b, penciclovir, peramivir, plerixafor, PRO 140, racivir, raltegrvir, ritonavir, ribavirin, rimantadine, rlipivirine, saquinavir, stampidine, stavudine, tenofovir, tipranavir, TNX-355, trifluridine, tromantadine, valaciclovir, valganciclovir, vicriviroc, vidarabione, viramidine, vivecon, zalcitabine, zanamivir, and zidovudine.

In one embodiment, the solid pharmaceutical compositions of the present invention comprise corticosteroid-containing granules. The corticosteroid-containing granules may be granules comprising corticosteroid crystals and a film-forming binder, e.g., prepared by granulation. The corticosteroid crystals can have an average particle size ranging from about 1-300 µm, for example about 1-50 µm, about 1-100 µm, about 1-150 µm, about 1-200 µm, about 1-250 µm, about 50-100 µm, about 50-150 µm, about 50-200 µm, about 50-250 µm, about 50-300 µm, about 100-150 µm, about 100-200 µm, about 150-200 µm, about 150-250 µm, about 150-300 µm, about 200-250 µm, about 200-300 µm, or about 250-300 µm.

In another embodiment, the corticosteroid may be in the form of crystals. Such crystals may have an average size in the sub-micron range (e.g., average particle size of about <1 µm), or may be nanoparticles (e.g., average particle size in the range of about 1-100 nm).

In yet another embodiment, the corticosteroid may be present in amorphous form, for example in association with a stabilizing agent which limits drug recrystallization, e.g., polyvinylpyrrolidone (PVP) (including homo- and copolymers of polyvinylpyrrolidone and homopolymers or copolymers of N-vinylpyrrolidone); crospovidone; gums; cellulose derivatives (including hydroxypropyl methylcellulose (HPMC), hydroxypropyl methylcellulose phthalate, hydroxypropyl cellulose, ethyl cellulose, hydroxyethylcellulose, sodium carboxymethyl cellulose, calcium carboxymethyl cellulose, sodium carboxymethyl cellulose, and others); dextran; acacia; homo- and copolymers of vinyllactam, and mixtures thereof, cyclodextrins; gelatins; hypromellose phthalate; sugars; polyhydric alcohols; polyethylene glycol (PEG); polyethylene oxides; polyoxyethylene derivatives; polyvinyl alcohol; propylene glycol derivatives and the like, sodium lauryl sulphate, Tween® surfactants, Eudragit® polymers; and combinations thereof.

The film-forming binder may comprise any suitable binder used in granulation. Non-limiting examples of suitable film-forming binders include water-soluble, alcohol-soluble or acetone/water soluble binders, e.g. polyvinylpyrrolidone (PVP), corn starch, polyethylene oxide, polyethylene glycol, hydroxypropyl methylcellulose (HPMC), methylcellulose, or hydroxypropylcellulose (HPC). The amount of film-forming binder in the corticosteroid-containing granules can range from about 0.5% to about 10%, including about 0.5%-1%, about 0.5%-2%, about 0.5%-5%, about 0.5%-7%, about 1%-2%, about 1%-5%, about 1%-7%, about 1%-10%, about 2%-5%, about 2%-7%, about 2%-10%, about 5%-7%, about 5%-10%, and about 7%-10%.

The corticosteroid-containing granules of the present invention may also include other pharmaceutically acceptable ingredients, for example, fillers or diluents. Non-limiting examples of other pharmaceutically acceptable ingredients for the corticosteroid-containing granules include, for example, mannitol, lactose, microcrystalline cellulose, potassium sulfate, calcium phosphate, modified starch, and mixtures thereof. The amount of other pharmaceutically acceptable ingredients (e.g. fillers or diluents) in the corticosteroid-containing granules can range from about 5%-80%, including about 5%-70%, about 5%-60%, about 5%-50%, about 5%-40%, about 5%-30%, about 5%-20%, about 5%-15%, about 5%-10%, about 10%-70%, about 10%-60%, about 10%-50%, about 10%-40%, about 10%-30%, about 10%-20%, about 10%-15%, about 20%-70%, about 20%-60%, about 20%-50%, about 20%-40%, about 20%-30%, about 20%-25%, about 30%-70%, about 30%-60%, about 30%-50%, about 30%-40%, about 30%-35%, about 40%-70%, about 40%-60%, about 40%-50%, about 40%-45%, about 50%-70%, about 50%-60%, about 50%-55%, about 60%-70%, or about 60%-65%.

In another embodiment, the corticosteroid-containing granules of the present invention can be in the form of corticosteroid-layered beads. Corticosteroid-layered beads comprise a core, e.g. a pharmaceutically acceptable sugar bead, coated with a corticosteroid layer. Such corticosteroid-layered beads can be prepared, for example, by dissolving or suspending corticosteroid in a polymeric binder solution, which is then sprayed or coated onto inert particles (e.g., sugar spheres or cellulose spheres (Celphere®)). Suitable polymeric binders include any of those disclosed herein, for example starches, modified celluloses (e.g., hydroxypropylcellulose, carboxymethylcellulose sodium), alginic acid, polyvinyl pyrrolidone (povidone), and mixtures thereof. The amount of corticosteroid in the corticosteroid layer, and the thickness of the corticosteroid layer can be modified to provide a therapeutically effective dose of corticosteroid. The corticosteroid-containing layer comprises about 90%-99% corticosteroid, and about 1% to about 10% binder.

The corticosteroid-containing granules of the present invention can be prepared by any suitable method. For example, the corticosteroid-containing granules can be prepared by granulation of corticosteroid crystals, one or more disintegrants, and one or more fillers (e.g., sugar alcohol, saccharide and/or microcrystalline cellulose) in a high shear granulator or a fluid-bed granulator using a solution of one or more polymeric binders, and dried in fluid bed equipment or on trays in a conventional oven to produce the corticosteroid-containing granules.

The solid pharmaceutical compositions of the present invention may include rapidly dispersing granules comprising a disintegrant and a sugar alcohol and/or a saccharide. The disintegrant-containing granules can include disintegrants or so-called super-disintegrants, e.g. crospovidone (crosslinked PVP), sodium starch glycolate, crosslinked sodium carboxymethyl cellulose, low substituted hydroxypropylcellulose, and mixtures thereof. The amount of disintegrant in the rapidly dispersing granules can range from about 1%-10%, or about 5%-10% of the total weight of the rapidly dispersing granules, including all ranges and subranges therebetween.

Sugar alcohols are hydrogenated forms of carbohydrates in which the carbonyl group (i.e., aldehyde or ketone) has been reduced to a primary or secondary hydroxyl group. Non-limiting examples of suitable sugar alcohols for the rapidly dispersing granules of the pharmaceutical compositions of the present invention include e.g. arabitol, isomalt, erythritol, glycerol, lactitol, mannitol, sorbitol, xylitol, maltitol, and mixtures thereof. The term "saccharide" is synonymous with the term "sugars" includes monosaccharides such as glucose, fructose, the lactose, and ribose; and disaccharides such as sucrose, lactose, maltose, trehalose, and cellobiose. In one embodiment, non-limiting examples of suitable saccharides for use in the compositions of the present invention include e.g. lactose, sucrose, maltose, and mixtures thereof. In another embodiment, the rapidly dispersing granules comprise at least one disintegrant in combination with a sugar alcohol. In another embodiment, the rapidly dispersing granules comprise at least one disintegrant in combination with a saccharide. In yet another embodiment, the disintegrant-containing granules comprise at least one disintegrant in combination with a sugar alcohol and a saccharide. The amount of sugar alcohol and/or saccharide in the rapidly dispersing granules ranges from about 99%-90%, or about 95%-90% of the total weight of the disintegrant-containing granules, including all ranges and subranges therebetween. In one embodiment, the average particle size of a sugar alcohol and/or saccharide is 30 µm or less, for example about 1-30 µm, about 5-30 µm, about 5-25 µm, about 5-20 µm, about 5-15 µm, about 5-10 µm, about 10-30 µm, about 10-25 µm, about 10-20 µm, about 10-15 µm, about 15-30 µm, about 15-25 µm, about 15-20 µm, about 20-30 µm, about 20-25 µm, or about 25-30 µm.

The corticosteroid-containing particles (e.g., crystals, granules, or drug-layered beads) of the solid pharmaceutical compositions of the present invention can also be coated with a taste-masking layer to improve the palatability of the composition. The corticosteroid-containing particles can be taste-masked by coating the corticosteroid-containing particles (e.g., crystals, granules, or drug-layered beads) with a water-insoluble polymer. Non-limiting examples of suitable water-insoluble polymers for the taste-masking layer include ethylcellulose, polyvinyl acetate (PVA), cellulose acetate (CA), cellulose acetate butyrate (CAB), methacrylate copolymers, such as those available under the tradename "EUDRAGIT" (e.g., type RL, RS, and NE30D), and combinations thereof.

In one embodiment, the water-insoluble polymer is ethylcellulose having a viscosity of about 90-110 cps when tested in an Ubbelohde viscometer as a 5 weight % 80:20 toluene/ethanol solution at 25° C.

In one embodiment, the solid pharmaceutical compositions of the present invention comprise about 25-35% of corticosteroid crystals, microencapsulated with a taste-masking layer comprising a water-insoluble polymer (e.g., ethylcellulose); about 60-70% of rapidly-dispersing granules (e.g., comprising crospovidone and mannitol); about 5% of additional disintegrant (e.g., crospovidone); about 1% of one or more flavors, and about 0.5%-1% of a sweetener (e.g., sucralose).

The method of producing drug-layered beads in one embodiment of the invention comprises dissolving or suspending corticosteroid in a polymeric binder solution and layering onto inert particles (50-100 mesh or 150-300 µm in diameter) such as sugar spheres or cellulose spheres (e.g., Celphere® CP-203) using a fluid-bed coater equipped with a bottom-spray Wurster insert. These corticosteroid-coated beads can then be taste-masked by fluid-bed coating or by solvent coacervation as described herein.

In another embodiment, the compositions of the present invention can comprise corticosteroid particles (e.g., crystals), coated with a taste-masking layer. The taste-masking layer (as described herein) can be applied to the corticosteroid particles by any suitable method, for example coacervation or fluidized bed coating methods. Alternatively, the compositions of the present invention can comprise a corticosteroid complexed with a cyclodextrin.

In one embodiment, the method of preparing the compositions of the present invention includes a taste-masking step. The taste-masked corticosteroid-containing particles of the compositions of the present invention (e.g., corticosteroid crystals, corticosteroid-containing microgranules or drug-layered beads) of the present invention can be prepared by various methods, including solvent coacervation with a water-insoluble polymer such as ethylcellulose. The water-insoluble polymer (e.g., ethylcellulose), a phase-inducer (e.g., polyethylene), and corticosteroid are loaded into a coacervation tank containing cyclohexane. The mixture in the tank is heated to about 80° C. to dissolve the ethylcellulose, and then slowly cooled under controlled conditions thereby causing phase-induced microencapsulation of corticosteroid particles by the ethylcellulose. Microencapsulation or coacervation refers to the process of applying a membrane by phase separation for imparting taste-masking (or sustained release) properties. Upon reaching ambient temperature, the suspension of microencapsulated corticosteroid particles are filtered, washed with fresh cyclohexane and dried to reduce residual solvent levels within acceptable limits (e.g., <4,000 ppm), in one embodiment less than 1,000 ppm. The coating weight of the microencapsulated corticosteroid particles can range from about 5% to about 30% including about 10%, 15%, 20%, and 25%, inclusive of all ranges and subranges therebetween. Examples of such a coacervation process are disclosed in U.S. Pat. Nos. 5,252,337, 5,639,475, 6,139,865 and 6,495,160.

Alternatively, the coacervation solution can comprise a mixture of the water-insoluble polymer (e.g., ethylcellulose) and a water-insoluble or gastrosoluble pore-former (e.g., calcium carbonate). The ratio of water-insoluble polymer to pore-former can range from about 50/50 to 95/05, including about 55/45, about 60/40, about 65/35, about 70/30, about 75/25, about 80/20, about 85/15, and about 90/10, including all ranges and subranges therebetween. The coating weight of the microencapsulated corticosteroid particles can range from about 5% to about 30% including about 10%, 15%, 20%, and 25%, inclusive of all ranges and subranges therebetween. In one embodiment, the coacervation step comprises suspending the drug-containing particles in a solution of water-insoluble ethylcellulose at 80° C. in the coacervation tank. During the cooling cycle, the micronized pore-former is introduced into the tank at a temperature of about 58° C., while constantly stirring the suspension to uniformly distribute the pore-former in the microcapsule-membrane, at the forming/hardening phase. Examples of such a coacervation process are disclosed in U.S. Patent Publication No. US 2006/0105038.

In one embodiment, the solid pharmaceutical composition of the present invention is in the form of an orally disintegrating tablet (ODT). In one such embodiment the ODT comprises drug particles and rapidly dispersing granules, wherein the drug particles comprise the corticosteroid, and the rapidly dispersing granules comprise a disintegrant and a sugar alcohol and/or saccharide. The drug particles may comprise, for example, corticosteroid crystals with or without a coating, corticosteroid-layered beads or granulates of corticosteroid with one more additional components. In certain embodiments the ODT is in the form of a wafer or film (for example those described in U.S. Pat. No. 6,534,549, U.S. Pat. No. 7,125,564, etc.).

In one embodiment of the present invention the solid composition comprises a lyophilized matrix, wherein the lyophilized matrix comprises corticosteroid and an excipient. Suitable excipients include mannitol, xylitol, sorbitol, maltol, maltitol, lactose, sucrose, maltose, and combinations thereof.

The amount of corticosteroid-containing granules in the solid compositions of the present invention can range from about 5% to about 50%, including about 5%, about 10%, about 15%, about 20%, about 25%, about 30%, about 35%, about 40%, about 45%, and about 50%, inclusive of all values, ranges, and sub-ranges therebetween. In one embodiment, the composition of the present invention is an ODT comprising about 30% by weight of corticosteroid-containing granules.

One embodiment of a method for producing pleasant tasting corticosteroid ODT formulations of the present invention, comprising corticosteroid microparticles with a mean particle size of about 100-400 µm, comprises (i) preparing drug-containing cores having corticosteroid crystals with a desired mean particle size, e.g., as microgranules, corticosteroid particles (e.g., crystals), or as drug-layered beads, (ii) preparing granules comprising a disintegrant, a sugar alcohol and/or a saccharide, and (iii) compressing a blend comprising the corticosteroid microparticles and the disintegrant granules, optionally with pharmaceutically acceptable flavorant(s), sweetener(s), other disintegrant(s), colorant(s) and/or compression aides such as microcrystalline cellulose in sufficient quantities into the ODT form using a tablet press, such as a rotary tablet press equipped with an external lubrication system to lubricate the punches and dies prior to compression. These ODT tablets rapidly disintegrate upon exposure to the saliva in the mouth into a smooth, easy-to-swallow suspension with no gritty aftertaste.

In another embodiment, the method for preparing ODT formulations of the present invention comprising corticosteroid microparticles with a mean particle size of about 100-400 µm can also include a unit process for taste-masking the corticosteroid-containing particles (e.g., corticosteroid crystals, corticosteroid-containing granules or drug-layered beads) by coacervation or fluid bed coating prior to blending and compression into ODT tablets. For example, corticosteroid crystalline material with an average particle size range of about 1-200 µm, more particularly about 50-150 µm can be coated with a taste-masking layer by either fluid-bed coating or solvent coacervation in accordance with other aspects of the invention. Corticosteroid crystalline material with a mean particle size of about 5-50 µm can also be taste-masked by solvent coacervation as described herein.

In another embodiment, the compositions of the present invention can be orally disintegrating tablets prepared by mixing corticosteroid microgranules or taste-masked corticosteroid microparticles, one or more flavoring agents, a sweetener, rapidly-dispersing microgranules, microcrystalline cellulose, and an additional disintegrant, and compressing this mixture into orally disintegrating tablets. The orally disintegrating tablets formed thereby rapidly disintegrate on contact with saliva in the buccal cavity, and have a pleasant taste (good creamy mouth feel) and provide rapid, substantially-complete release of the dose in the stomach.

In yet another embodiment, the compositions of the present invention may be orally disintegrating tablets formed by compressing a composition comprising corticosteroid-containing particles, rapidly-dispersing granules, and optionally flavoring agents, sweeteners, and other pharmaceutically acceptable excipients in a tablet press equipped with an externally lubricating system to pre-lubricate dies and punches, thereby providing a tablet formulation otherwise free of lubricant. The orally disintegrating tablets thus produced typically exhibit sufficient hardness and sufficiently low friability to be suitable for packaging in HDPE bottles and push-through film backed or peel-off paper backed blister packs using conventional equipment for storage, transportation and commercial distribution.

In another embodiment, a method of manufacturing orally disintegrating tablets of the present invention comprises the following steps: (a) preparing corticosteroid-containing microgranules by granulating crystalline corticosteroid material having an average particle size of about 5-50 µm and one or more diluents/fillers such as lactose, mannitol, microcrystalline cellulose and mixtures thereof, with a polymeric binder in a high-shear granulator or a fluid-bed coater; (b) granulating one or more sugar alcohols and/or saccharides, each having an average particle diameter of not more than about 30 µm, with a disintegrant such as crospovidone, using water or an alcohol-water mixture in a conventional granulator, and drying the granulate in fluid-bed equipment or a conventional oven to produce rapidly-dispersing microgranules with an average particle size of not more than about 400 µm, as described in U.S. Patent Publication No. US 20050232988; filed Apr. 19, 2004; (c) blending the corticosteroid microgranules of step (a) with one or more flavoring agents, a sweetener, microcrystalline cellulose, additional disintegrant, and the rapidly-dispersing microgranules of step (b); and (d) compressing the blend of step (c) into tablets using e.g. a conventional rotary tablet press equipped with an external lubrication system to pre-lubricate the dies and punches.

In another embodiment, a method of manufacturing orally disintegrating tablets of the present invention comprises the following steps: a) preparing a drug-containing core particle (e.g., corticosteroid crystals, drug-layered beads, or corticosteroid-containing microgranules) by granulating the drug and optionally one or more diluents/fillers such as lactose, mannitol, microcrystalline cellulose and mixtures thereof with a polymeric binder in a high-shear granulator or a fluid-bed coater, or drug-layering on an inert particle (60-100 mesh sugar sphere or cellulose sphere, e.g., Celphere® CP-203) from a solution/suspension comprising a polymeric binder and the drug in a fluid-bed coater and optionally applying a seal-coat (e.g., Opadry® Clear); b) taste-masking core particles by microencapsulation, e.g. by solvent coacervation or fluid-bed coating with a water-insoluble polymer such as ethylcellulose, or with a mixture of a water-insoluble functional polymer and a water-soluble/gastrosoluble pore-former (e.g., ethylcellulose and sodium chloride or calcium carbonate at a ratio ranging from about 50/50 to 95/5) to produce pleasant-tasting microparticles with a desired particle size distribution (e.g., an average particle size of not more than about 400 nm, or an average particle size of not more than about 300 μm); c) granulating one or more sugar alcohols and/or saccharides, each of which has an average particle diameter of not more than about 30 μm, with a disintegrant such as crospovidone, as disclosed herein; d) blending the taste-masked microparticles of step (b) with one or more flavoring agents, a sweetener, microcrystalline cellulose, additional disintegrant, and rapidly-dispersing microgranules of step (c); and e) compressing the blend of step (d) into tablets using e.g. a conventional rotary tablet press equipped with an external lubrication system to pre-lubricate the dies and punches.

EXAMPLE 1

Fluticasone Propionate Microgranules A

Mannitol 25 (91.2% w/w) and Crospovidone XL-10 (4.8% w/w) at a ratio of 95/5 are co-milled individually by passing the mixture through a Comil® milling apparatus, equipped with 0.225" spacers, at a speed of about 1400-1500 rpm. The mannitol, crospovidone, and fluticasone propionate (4% w/w) crystalline material are blended for about 3-5 minutes to mix the ingredients. A Glatt GPCG-3 fluid-bed apparatus equipped with a top spray granulation chamber and a granulation bowl is charged with the pre-blend of mannitol, crospovidone, and fluticasone propionate (batch size: 1500 g) and granulated by spraying purified water (nozzle: 1.2 mm tip) at an atomization pressure of about 1.25 bar and at a spray rate of 30-50 mL/min and an outlet temperature of >70° C. and at a product temperature of >33° C. The wet mass is dried until the moisture level (the percent loss on drying) is less than about 1%.

Tableting:

A Hata production tablet press equipped with a vacuum transfer system, tablet de-duster, a metal detector, and a Matsui Ex-lube system were set up according to standard operating procedures. Magnesium stearate was used as a processing aid, i.e., to externally lubricate the punch and die surfaces and was therefore present in only trace amounts on the tablets. The weight range for the tablets was typically ±5% of the target tablet weight. The Ex-lube system was started to ensure that the lubricant was spraying properly when the tablet press was running. The tableting parameters, such as fill depth (mm), pre-compression position (mm or kN) and main compression position (mm or kN) were adjusted on the press in order to produce 4 mg tablets that meet the exemplary specifications listed below:

TABLE

Tablet Parameters

| Parameter | Target | Range |
| --- | --- | --- |
| Weight (mg) | 100 | 95-105 |
| Thickness (mm) | 2.4 | 2.0-2.8 |
| Hardness (N) | 28 | 8-48 |
| Friability | NMT 0.6% | 1.0% |
| Weight 10 tablets (g) | 1.0 g | 0.96-1.04 |

Following the successful set-up, the press was run in 'Automatic Mode' until completion. During the run, tablets were sampled periodically to ensure that the tablets produced would meet the specifications listed above.

The tablets are tested in the USP <701> Disintegration test and disintegrate in about 60 seconds or less.

EXAMPLE 2

A liquid is prepared by mixing 89.8% of 95% ethanol, by weight 5% ethylcellulose, 0.2% by weight oleic acid and 5% fluticasone propionate. Upon dabbing on to a mucosal surface a film is formed which adheres readily to skin or mucosal tissues.

An ethyl alcohol based gel is prepared by mixing the following components: 67% by weight of 95% ethyl alcohol; 8% by weight ethylcellulose; 2% by weight hydroxypropylcellulose; 2% by weight polyacrylic acid; 14% by weight menthol; 5% by weight water USP; and 2% by weight fluticasone propionate. A smooth, slightly opaque and sticky gel is formed.

The film, resulting from the application of this gel to a mucosal surface adheres to the surface and requires mechanical effort for its removal.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. An oral, substantially non-aqueous liquid pharmaceutical composition comprising a corticosteroid, a pharmaceutically acceptable non-aqueous liquid, and a phase change agent dissolved or suspended in the non-aqueous liquid, wherein after oral administration to a patient, said composition undergoes a change in physical properties of the composition upon contact with the upper gastrointestinal tract of said patient, whereby contact of the corticosteroid with the upper gastrointestinal tract of the patient is enhanced and/or prolonged.

2. The liquid pharmaceutical composition of claim 1, wherein the non-aqueous liquid is selected from the group consisting of pharmaceutically acceptable alcohols, oils, glycols, glycol ethers, pyrrolidones, polyethylene glycols, N-methyl-2-pyrrolidone, 2-pyrrolidone, glycerol, tetraglycol, glycerol formal, solketal, ethyl acetate, ethyl lactate, ethyl butyrate, dibutyl malonate, tributyl citrate, tri-n-hexyl acetylcitrate, diethyl succinate, diethyl glutarate, diethyl malonate, triethyl citrate, triacetin, tributyrin, diethyl carbonate, propylene carbonate, acetone, methyl ethyl ketone, dimethyl sulfoxide, dimethyl sulfone, tetrahydrofuran, caprolactam, N,N-diethyl-m-toluamide, 1-dodecylazacycloheptan-2-one, 1,3-dimethyl-3,4,5,6-tetrahydro-2(1H)-pyrimidinone, and combinations thereof.

3. The liquid pharmaceutical composition of claim 2, wherein the non-aqueous liquid is selected from the group consisting of alcohols, oils, glycols, glycol ethers, pyrrolidones, liquid polyethylene glycols, glycerol and combinations thereof.

4. The liquid pharmaceutical composition of claim 3, wherein the non-aqueous liquid is selected from the group consisting of ethanol, glycerol, propylene glycol, glycerides, polyethylene glycol with a molecular weight between about 200 and 600, and combinations thereof.

5. The liquid pharmaceutical composition of claim 1, wherein after administration to a patient, said composition precipitates onto the mucosa of the gastrointestinal tract of the patient, whereby deposition of the corticosteroid onto the mucosa of the gastrointestinal tract is enhanced and/or prolonged.

6. The liquid pharmaceutical composition of claim 1, wherein after administration to a patient, said composition forms a gel on contact with the mucosa of the gastrointestinal tract of the patient, whereby the deposition of the corticosteroid onto the mucosa of the gastrointestinal tract is enhanced and/or prolonged.

7. The liquid pharmaceutical composition of claim 1, wherein after administration to a patient, said composition increases in viscosity upon contact with the mucosa of the gastrointestinal tract of the patient, whereby the residence time of the corticosteroid on the mucosa of the intestinal tract is prolonged.

8. The liquid pharmaceutical composition of claim 1, wherein said phase change agent is a poorly water-soluble polymer.

9. The liquid pharmaceutical composition of claim 1, wherein said phase change agent is a thermosensitive polymer whose aqueous viscosity increases in the range of about 15-40° C.

10. The liquid pharmaceutical composition of claim 1, wherein said phase change agent increases in viscosity upon contact with fluids of the oropharynx.

11. The liquid pharmaceutical composition of claim 1, wherein the phase change agent is a polymer selected from the group consisting of poly(N-isopropylacrylamide), poly(ethylene glycol-(DL-lactic acid-co-glycolic acid)-ethylene glycol) and mixtures thereof.

12. The liquid pharmaceutical composition of claim 1, wherein said corticosteroid is selected from the group consisting of budesonide, fluticasone, flunisolide, ciclesonide, mometasone, tixocortol, beclomethasone, and salts, solvates, and esters thereof.

13. The liquid pharmaceutical composition of claim 6, wherein said non-aqueous liquid is water-miscible and said phase change agent is a bio-gelling polymer having a low water-solubility.

14. The liquid pharmaceutical composition of claim 13, wherein said water-miscible liquid is selected from the group consisting of ethanol, isopropyl alcohol, N-methyl-2-pyrrolidone, 2-pyrrolidone, glycerol, propylene glycol, liquid polyethylene glycol, tetraglycol, glycerol formal, solketal, ethyl acetate, ethyl lactate, diethyl carbonate, propylene carbonate, acetone, methyl ethyl ketone, dimethyl sulfoxide, dimethyl sulfone, tetrahydrofuran, and combinations thereof.

15. The liquid pharmaceutical composition of claim 13, wherein said bio-gelling polymer is selected from the group consisting of polylactides, polyglycolides, polycaprolactones, polydioxannones, polycarbonates, polyhydroxybutyrates, polyalkyene oxalates, polyanhydrides, polyamides, polyesteramides, polyurethanes, polyacetals, polyketals, polyorthocarbonates, polyphosphazenes, polyhydroxyvalerates, polyalkylene succinates, poly(malic acid), poly(amino acids), chitin, chitosan, polyorthoesters, cellulose derivatives, cellulose esters, methacrylic acid and methacrylate polymers, and copolymers, terpolymers and mixtures thereof.

16. The liquid pharmaceutical composition of claim 15, wherein said bio-gelling polymer is ethylcellulose.

17. The liquid pharmaceutical composition of claim 10, wherein said increase in viscosity is at least 50%.

18. The liquid pharmaceutical composition of claim 10, wherein said increase in viscosity is at least 100%.

19. The liquid pharmaceutical composition of claim 10, wherein said increase in viscosity is at least 200%.

20. A method for treating an inflammatory condition of the upper gastrointestinal tract comprising orally administering to an individual in need thereof an oral substantially non-aqueous liquid pharmaceutical composition comprising a corticosteroid, a pharmaceutically acceptable liquid, and a phase change agent dissolved or suspended in the non-aqueous liquid, wherein after oral administration to a patient, said composition undergoes a change in physical properties of the composition upon contact with the upper gastrointestinal tract of said patient, whereby contact of the corticosteroid with the upper gastrointestinal tract of the patient is enhanced and/or prolonged.

21. The method of claim 20, wherein said condition is eosinophilic esophagitis.

22. The method of claim 20, wherein said inflammation comprises inflammation of the glottis, epiglottis, tonsils, or oropharynx.

23. The method of claim 20, wherein said condition is viral or bacterial pharyngitis.

24. The method of claim 20, wherein said condition is gastroesophageal reflux disease (GERD), non-erosive reflux disease (NERD) or erosive esophagitis.

25. The liquid pharmaceutical composition of claim 1, wherein the change in physical properties occurs upon contact with the esophagus.

* * * * *